(12) United States Patent
Tanner et al.

(10) Patent No.: US 11,466,264 B2
(45) Date of Patent: Oct. 11, 2022

(54) IN VITRO CLEAVAGE OF DNA USING ARGONAUTE

(71) Applicant: New England Biolabs, Inc., Ipswich, MA (US)

(72) Inventors: Nathan Tanner, Peabody, MA (US); Eric Hunt, Danvers, MA (US)

(73) Assignee: New England Biolabs, Inc., Ipswich, MA (US)

( * ) Notice: Subject to any disclaimer, the term of this patent is extended or adjusted under 35 U.S.C. 154(b) by 428 days.

(21) Appl. No.: 16/018,806

(22) Filed: Jun. 26, 2018

(65) Prior Publication Data

US 2019/0002868 A1    Jan. 3, 2019

Related U.S. Application Data

(60) Provisional application No. 62/526,019, filed on Jun. 28, 2017.

(51) Int. Cl.

| | |
|---|---|
| *C12N 15/10* | (2006.01) |
| *C07K 14/195* | (2006.01) |
| *C12N 9/22* | (2006.01) |
| *C12N 15/113* | (2010.01) |
| *C12N 9/12* | (2006.01) |
| *C12N 15/11* | (2006.01) |
| *C12N 15/90* | (2006.01) |

(52) U.S. Cl.
CPC .......... *C12N 15/102* (2013.01); *C07K 14/195* (2013.01); *C12N 9/1252* (2013.01); *C12N 9/22* (2013.01); *C12N 15/11* (2013.01); *C12N 15/113* (2013.01); *C12N 15/90* (2013.01); *C12N 2310/14* (2013.01)

(58) Field of Classification Search
CPC .................................................. C12N 15/102
See application file for complete search history.

(56) References Cited

U.S. PATENT DOCUMENTS

| | | | | |
|---|---|---|---|---|
| 6,852,832 | B1 * | 2/2005 | Kowalczykowski | C07H 21/02 530/358 |
| 2014/0038241 | A1 | 2/2014 | Zhou et al. | |
| 2015/0023943 | A1 | 1/2015 | Cox et al. | |
| 2015/0089681 | A1 * | 3/2015 | Van Der Oost | G01N 33/542 800/25 |

FOREIGN PATENT DOCUMENTS

| | | | | |
|---|---|---|---|---|
| WO | 2016028843 | A2 | 2/2016 | |
| WO | 2016109255 | A1 | 7/2016 | |
| WO | WO-2016109255 | A1 * | 7/2016 | ......... C12N 15/1031 |
| WO | 2016161375 | A2 | 10/2016 | |
| WO | WO-2016161375 | A2 * | 10/2016 | ........... C12Q 1/6806 |
| WO | 2017107898 | A2 | 6/2017 | |
| WO | WO-2017107898 | A2 * | 6/2017 | ........... C07K 14/195 |

OTHER PUBLICATIONS

Dabrowski et al., Identification and characterization of singlestranded-DNA-binding proteins from Thermus thermophilus and Thermus aquaticus—new arrangement of binding domains, 2002, Microbiology, vol. 148, pp. 3307-3315. (Year: 2002).*
Dabrowski et al. (2002) Identification and characterization of single stranded-DNA-binding proteins from Thermus thermophilus and Thermus aquaticus—new arrangement of binding domains. Microbiology, 148:3307-3315 (Year: 2002).*
Olszewski et al. (2010) Characterization of exceptionally thermostable single-stranded DNA-binding proteins from Thermotoga maritima and Thermotoga neapolitana. BMC Microbiology, 10(260):pp. 1-10 (Year: 2010).*
M2402S Tth RecA (New England Biolab's Tth RecA, Thermus thermophilus RecA homology, Certificate of Analysis, Product No. M2402S, Lot: 0061207, dated 2014, 1 page) (Year: 2014).*
New England Biolab's Extreme Thermostable Single-Stranded DNA Binding Protein, Certificate of Analysis, Product No. M2401S, Lot: 0031206, dated 2014, 1 page (Year: 2014).*
Vidyasagar et al., Purification and characterization of a thermostable, haloalkaliphilic extracellular serine protease from the extreme halophilic archaeon Halogeometricum borinquense strain TSS101, Archaea (2006) 1, 51-7 (Year: 2006).*
Liao et al., Morphological and proteomic analysis of biofilms from the Antarctic archaeon, Halorubrum lacusprofundi. Sci Rep (2016) 6:37454) (Year: 2016).*
Ward et al., A Natural View of Microbial Biodiversity within Hot Spring Cyanobacterial Mat Communities. Microbiology and Molecular Biology Reviews, Dec. 1998, p. 1353-1370 (Year: 1998).*
Lisitskaya et al., DNA interference and beyond: structure and functions of prokaryotic Argonaute proteins. Nat Commun. (2018) 9: 5165 (Year: 2018).*
Kelman et al., Isolation and Characterization of a Split B-type DNA Polymerase from the Archaeon Methanobacterium thermoautotrophicum DeltaH. Journal of Biological Chemistry, 1999. 274(40), 28751-28761; p. 28756 (Year: 1999).*
De Leon et al., Archaeal and bacterial communities in three alkaline hotsprings in Heart Lake Geyser Basin, Yellowstone National Park. Frontiers in Microbiology, 2013. 4(330), 1-10 (Year: 2013).*
Wasserfallen et al., Phylogenetic analysis of 18 thermophilic Methanobacterium isolates supports the proposals to create a new genus . . . Intl J. Systematic and Evol. Micro. (2000), 50, 43-53 (Year: 2000).*

(Continued)

*Primary Examiner* — Neil P Hammell
*Assistant Examiner* — Catherine Konopka
(74) *Attorney, Agent, or Firm* — New England Biolabs, Inc

(57) ABSTRACT

Methods, kits and compositions, in some embodiments, may include a thermostable DNA guided Argonaute protein for example TtAgo, a thermostable single-stranded DNA binding protein (SSB) for example, ET SSB, and, optionally, a strand-displacing polymerase. A SSB may allow (a) Argonaute/guide DNA complexes to substantially enhance cleavage efficiency of single- and double-stranded DNA substrates; (b) the use of longer guide DNAs (e.g., guide DNAs that are at least 24 nucleotides in length) and/or (c) increases in the sequence specificity of Argonaute-mediated binding and cleavage reactions.

23 Claims, 8 Drawing Sheets
(1 of 8 Drawing Sheet(s) Filed in Color)

(56) References Cited

OTHER PUBLICATIONS

Wang et al., Structure of an argonaute silencing complex with a seed-containing guide DNA and target RNA duplex. Nature 2008. Dec. 18;456(7224):921-6 (Year: 2008).*
Grasso and Tell. Base excision repair in Archaea: Back to the future in DNA repair DNA Repair, 2014. 21:148-157 (Year: 2014).*
Antranikian et al., Diversity of bacteria and archaea from two shallow marine hydrothermal vents from Vulcano Island. Extremophiles (2017) 21:733-742 (Year: 2017).*
GenBank assembly accession: GCA_002754935.1, Nov. 6, 2017 (Year: 2017).*
GenBank assembly accession: GCA_000008645.1, Dec. 22, 1999 (Year: 1999).*
GenBank Accession: WP_012082537, BCT Oct. 13, 2019 (Year: 2019).*
Methanothermobacter "replication protein A"—Protein—NCBI search results (Year: 2021).*
NCBI Conserved Domain Search for on [gi|1275726087|ref|WP_099799291|], Retrieved Nov. 19, 2021. (Year: 2021).*
Swarts et al., Argonaute of the archaeon Pyrococcus furiosus is a DNA-guided nuclease that targets cognate DNA. Nucleic Acids Res (2015), 43(10), 5120-9 (Year: 2015).*
GenBank: CP003685.1, Pyrococcus furiosus COM1, complete genome, Published Jan. 20, 2014 (Year: 2014).*
M2401S ET SSB (New England Biolab's Extreme Thermostable Single-Stranded DNA Binding Protein, Certificate of Analysis, Product No. M2401S, Lot: 0031206, dated 2014, 1 page) (Year: 2014).*
Swarts, et al.. Nucleic Acids Research, 2015, 43, 10, 5120-5129.
Enghiad, et al ACS Synth Biol 6, 752-757 (2017).
Willkomm, S. et al., 2015. Life (Basel, Switzerland), 5(1), pp. 538-553.
New England Biolabs M2401 Datasheet—Lot 0031509 Exp 9-17.
Olszewski, et al., BMC Microbiology, 2010, 10:260 (10 pages).

* cited by examiner

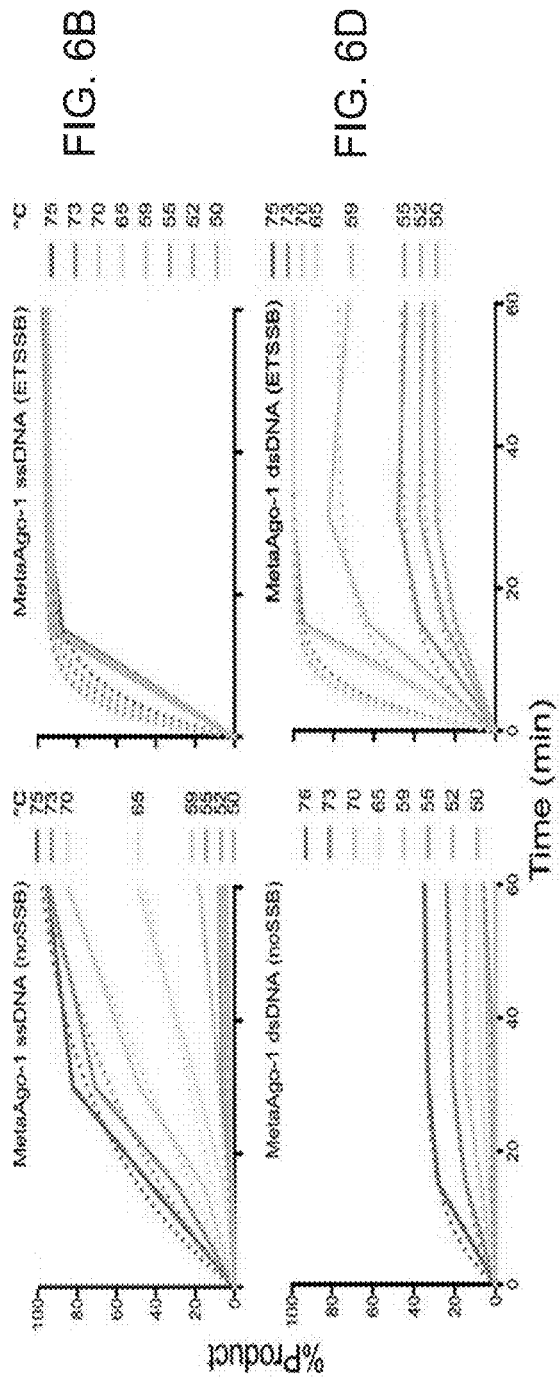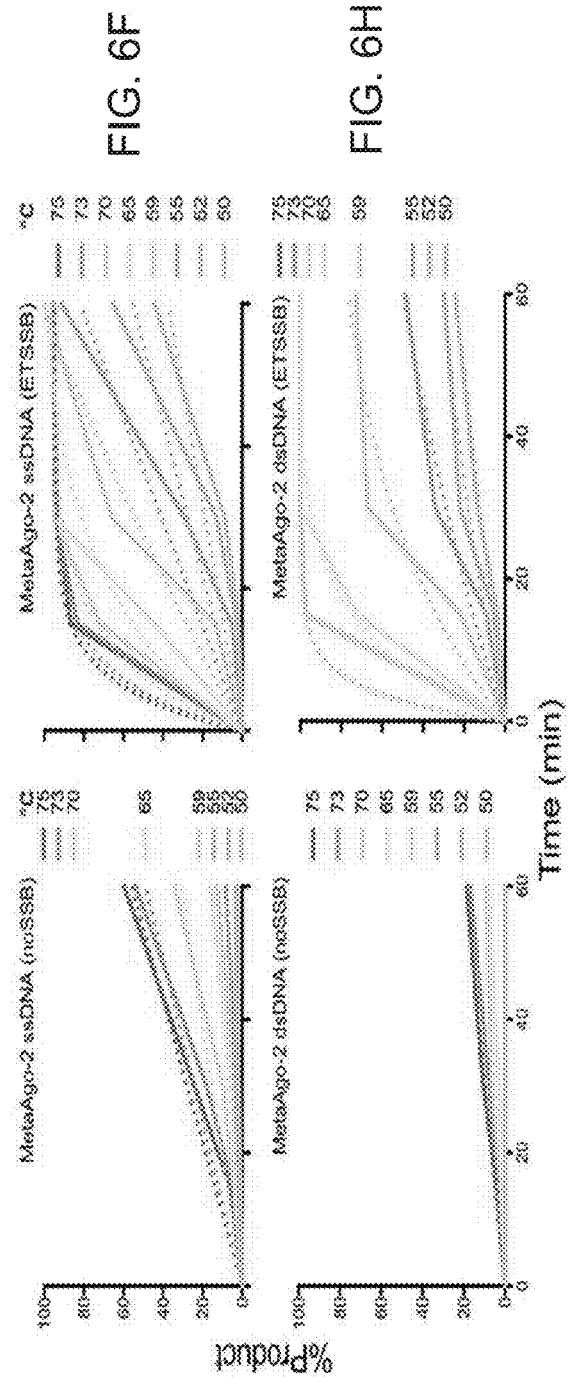

IN VITRO CLEAVAGE OF DNA USING ARGONAUTE

CROSS-REFERENCE

This application claims the benefit of U.S. Provisional Application Ser. No. 62/526,019, filed on Jun. 28, 2017, which application is incorporated by reference herein in its entirety.

BACKGROUND

Recognition of specific nucleic acid sequences is a critical requirement for a wide range of molecular biology and biotechnology applications. Sequences of interest can be enriched from a population, modified or acted upon by nucleic acid enzymes, detected for diagnostic applications, and/or used as substrates for subsequent nucleic acid manipulation. The recognition of a desired sequence can be facilitated by enzymes referred to as "Argonautes" which are used by cells to find and defend against exogenous nucleic acids through oligonucleotide-guided binding and cleavage.

When used in vitro, Argonaute proteins can be adapted for targeting a DNA or RNA molecule, but they are limited in utility as they apparently only bind to single-stranded templates. One example of a DNA guided Argonaute is from *Thermus thermophilus*, TtAgo. TtAgo has been found to be unable to cleave linear double-stranded DNA (dsDNA) (Swarts, et al. Nature 507, 258-261 (2014)). Moreover, even at higher temperatures as much as 90° C.–100° C., thermostable Argonautes from archaea do not cleave plasmid DNA unless complete separation of the dsDNA into single strands had been achieved (Enghiad, et al ACS Synth Biol 6, 752-757 (2017)).

Additional problems described for DNA guided Argonautes include a slow cycle of binding and cleavage which requires long incubation times to achieve cleavage of single-stranded DNA (ssDNA). Argonautes have a narrow range of usable guide molecule length. In WO 2016/161375, enhanced cleavage rates using archaeal and bacterial Argonautes require including a recruiting domain of 8 nucleotides, a stabilizing domain of 4 nucleotides and a guide sequence which together form a complex that enhances the rate of cleavage by Argonaute. The reference further describes that dsDNA can be cleaved if two guided Argonautes are used each with a different guide DNA or RNA. Other proteins produced in cells to cleave nucleic acids include Cas9. However these proteins are significantly different from Argonaute. For example, Cas9 utilizes an RNA guide and not a DNA guide required by Argonaute, and is limited to certain sequences that contain a specific protospacer adjacent motif (PAM) sequence whereas Argonaute can be targeted to any sequence. Moreover, Cas9 contains two nuclease domains and is capable of cleaving dsDNA without requiring additional protein reagents.

SUMMARY

Among other things, it is shown herein that the addition of single-stranded DNA binding protein (SSB) allows (a) Argonaute/guide DNA complexes to substantially enhance efficiency of cleavage of single- and double-stranded DNA substrates; (b) the use of longer guide DNAs (e.g., guide DNAs that are at least 24 nucleotides in length) and (c) increases in the sequence specificity of Argonaute-mediated binding and cleavage reactions.

In some embodiments, a composition is provided. This composition may comprise a thermostable DNA guided Argonaute protein for example TtAgo and a thermostable SSB for example, ET SSB (Extreme Thermostable Single-Stranded DNA Binding Protein). The composition may further include a strand-displacing polymerase.

The composition may further include a guide DNA where for example, the guide DNA is 16-21 nucleotides in length or at least 22 nucleotides. Embodiments may also include primers, and/or substrates for immobilization of the Argonaute protein such as beads.

The various embodiments of the composition may be included in a kit. The kit may also include a reaction buffer. The components in the kit may be in the same or different tubes.

In one embodiment, a method is provided for nicking or cleaving a nucleic acid substrate at a target sequence, comprising: combining a thermostable DNA guided Argonaute protein, a thermostable SSB, a guide DNA and the nucleic acid substrate containing the target sequence that is complementary to at least part of the guide DNA, to produce a reaction mix; incubating the reaction mix to cleave the substrate DNA at the target sequence; and nicking or cleaving the nucleic acid substrate.

In one aspect of this embodiment, the nucleic acid substrate is a dsDNA substrate and cleaving of a strand of the dsDNA substrate results in nicked DNA.

In another aspect, the dsDNA substrate is eukaryotic genomic dsDNA.

In another aspect, the method further comprises cleaving the opposing strand of the substrate at the complement of the target sequence, thereby creating a double-stranded break or two nicks in the dsDNA substrate.

In another aspect, the nicking is performed under isothermal conditions.

In another aspect, substantially complete cleavage of the substrate occurs within 1 hour.

In another embodiment, a method is provided for copying a nucleic acid substrate, comprising: combining a thermostable DNA guided Argonaute protein, a thermostable SSB, the nucleic acid substrate that comprises a target sequence, a strand-displacing polymerase, and a guide DNA that is complementary to the target sequence, to produce a reaction mix; incubating the reaction mix so that a strand of the nucleic acid substrate provides a template for the polymerase, and extending (i) the 3' end of the guide DNA (ii) a separate primer that hybridizes to a site that is proximal to the target sequence or (iii) the 3' end formed by the Argonaute induced nick; and copying the nucleic acid substrate.

In one aspect, the Argonaute protein is catalytically inactive in (i) or (ii).

In one aspect, the Argonaute protein is catalytically active in (ii) or (iii).

In another aspect, the nucleic acid substrate is dsDNA.

In another aspect, copying or amplifying is performed under isothermal conditions.

In another aspect, the guide DNA is at least 24 nucleotides.

In another aspect, the reaction mix further comprises a second guide DNA complementary to a second target sequence that is proximal on the opposite strand to a first target sequence, and wherein the incubation step results in extension of the second guide DNA using the opposing strand as a template, thereby resulting in copying of both strands of the nucleic acid substrate between the first and the second guide DNA.

In general, a method is provided for identifying a polymorphism, comprising: combining a DNA guided thermostable Argonaute protein, a thermostable SSB, an allele-specific guide DNA, and a nucleic acid substrate that has a polymorphism in the region corresponding to nucleotides 12-15 of the guide DNA, to produce a reaction mix; incubating the reaction mix to cleave the nucleic acid substrate; and detecting cleavage of the nucleic acid substrate, wherein cleavage indicates the allele of the polymorphism.

In one aspect, the nucleic acid substrate is a dsDNA substrate.

In an embodiment, a method is provided for enriching for target DNA in a mixture that contains target DNA and non-target DNA, comprising combining an inactive Argonaute protein, an SSB, a guide DNA for hybridizing with target DNA and a DNA substrate that comprises a target sequence that is complementary to at least part of the guide DNA, to produce a reaction mix; and immobilizing the Argonaute protein with the guide DNA hybridized to the target sequence by means of a binding protein such as an antibody and a substrate suitable for manipulation such as a bead. The method may further include enriching for the target sequence by heating up the preparation to allow denaturation of the guide DNA:target DNA duplex.

These and other uses are described in greater detail below.

BRIEF DESCRIPTION OF THE FIGURES

The patent or application file contains at least one drawing executed in color. Copies of this patent or patent application publication with color drawings will be provided by the office upon request and payment of the necessary fee.

The skilled artisan will understand that the drawings, described below, are for illustration purposes only. The drawings are not intended to limit the scope of the present teachings in any way.

FIG. 1A shows that native TtAgo, in the absence of ET SSB, acts on low (30%) GC content ssDNA substrates more readily than medium (50%) to high (70%) GC content ssDNA substrates, and is unable to act on dsDNA substrates.

FIG. 1B shows that the addition of 310 nM of ET SSB to the reaction increases activity on all GC content ssDNA targets and increases the activity of Argonaute on dsDNA substrates. Equivalent results are obtained using the same concentrations of ET SSB with archaeal Argonaute from PfAgo.

FIG. 1C shows that the addition of 940 nM of ET SSB to the reaction increases activity on all GC content ssDNA targets and increases the activity of Argonaute on dsDNA substrates. Equivalent results are obtained using the same concentrations of ET SSB with archaeal Argonaute from PfAgo.

FIG. 1D shows that the addition of 1.3 µM of ET SSB to the reaction increases activity on all GC content ssDNA targets and enables equivalent activity on dsDNA substrates.

FIG. 2A shows the combination of native TtAgo without ET SSB and with ET SSB using varying lengths of 5'-phosphorylated DNA guides to cleave ssDNA substrates. In the absence of ET SSB, guides for ssDNA substrates from 16-19 nucleotides are the most efficient, but activity drops off rapidly for longer guides. The addition of ET SSB increases the range of guides while maintaining an equivalent high degree of catalytic activity throughout.

FIG. 2B shows a similar trend for archaeal PfAgo acting on ssDNA substrates.

FIG. 2C shows that TtAgo with ET SSB can also utilize a range of guide lengths, from 16-21 nucleotides to most efficiently cleave dsDNA substrates.

As shown, Argonautes are composed of four domains—being the N-terminal (N), Piwi-Argonaute-Zwille (PAZ), middle (MID), and P-element-induced wimpy testis (PIWI) domains—which are connected in some arrangements by structured linker regions. Argonautes possessing this structural layout, which include prokaryotic (e.g. TtAgo) and eukaryotic (e.g. human hAgo2) Argonautes, are considered "long." However, there also exists a class of "short" Argonautes which only possess MID and PIWI domains (Willkomm, et al., 2015. (Basel, Switzerland), 5(1), pp. 538-553). The 5' end of the guide is sequestered in a region of the MID domain. While the residues involved in this binding are somewhat conserved, some marked differences exist between eukaryotic Argonautes like hAgo2 and prokaryotic Argonautes like TtAgo. The 3' end of the guide is bound by the PAZ domain. The catalytic region of Argonautes is an RNase H-like fold located in the PIWI domain, which utilized a conserved DEDX (X=D or H) tetrad for catalysis. Mutations to these residues renders the Argonaute inactive.

Figure 5:
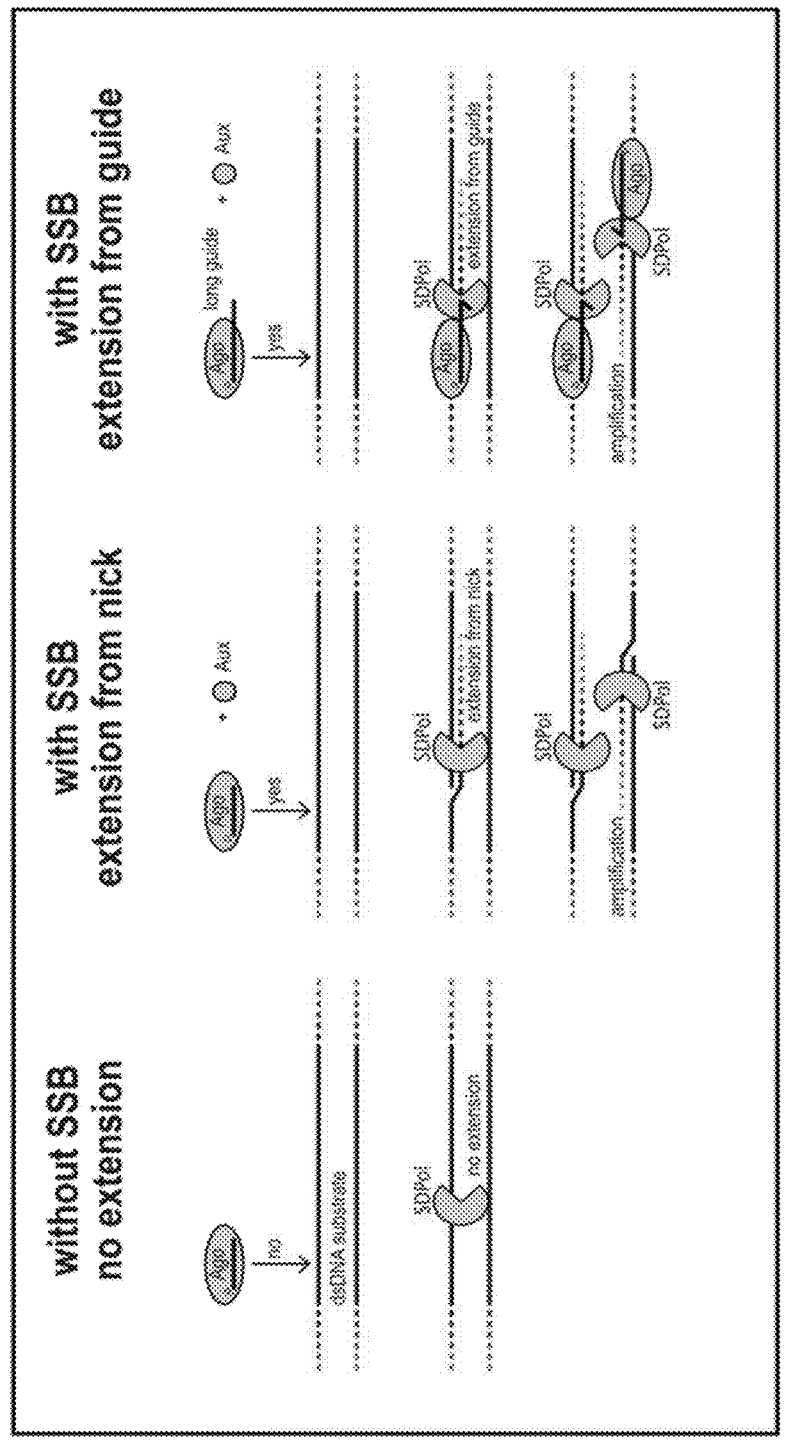

FIG. 5 schematically illustrates how Argonaute can be used to copy one or both strands of a dsDNA substrate. In this illustration, SDPol is a strand-displacing polymerase and "Aux" is an SSB. The left side of the figure illustrates the standard conditions of an Argonaute reaction, where the guide-Ago complex cannot access its target in dsDNA. By including a SSB dsDNA can be accessed by the Ago and amplification enabled by two distinct mechanisms: in the middle panel, the guided-Ago binds its target sequence and creates a nick through its inherent nuclease activity. This nick can serve as a substrate for the SDPol, which displaces downstream DNA and recreates the nicking target site to be re-used in the next reaction cycle as in the strand displacement amplification (SDA) reaction. On the right, use of a long guide, also enabled by SSB, creates an initiation site for the SDPol where the 3' end of the long guide is the DNA primer for polymerase activity. Extension and displacement by SDPol produces copies of the DNA target sequence through subsequent cycles of Ago-guide priming and SDPol extension.

FIG. 6A-6H show the effect of adding SSB to Argonaute proteins to achieve cleavage of dsDNA and ssDNA at various times and temperatures. Two prokaryotic Argonautes encoded by DNA derived from metagenomic material from an environmental hot spring source (MetaAgo-1 and MetaAgo-2) were selected. Consistent with TtAgo, they both exhibited increased reaction kinetics and activity on ssDNA targets (up to 10-fold increase) and dsDNA targets (up to >100-fold increase) in the presence of thermostable SSB over a 60 minute time period. Additionally, the addition of thermostable SSB allows these reactions to take place at lower temperature (to 50° C.) than possible when using the Argonaute alone (65° C.).

Figure 7:
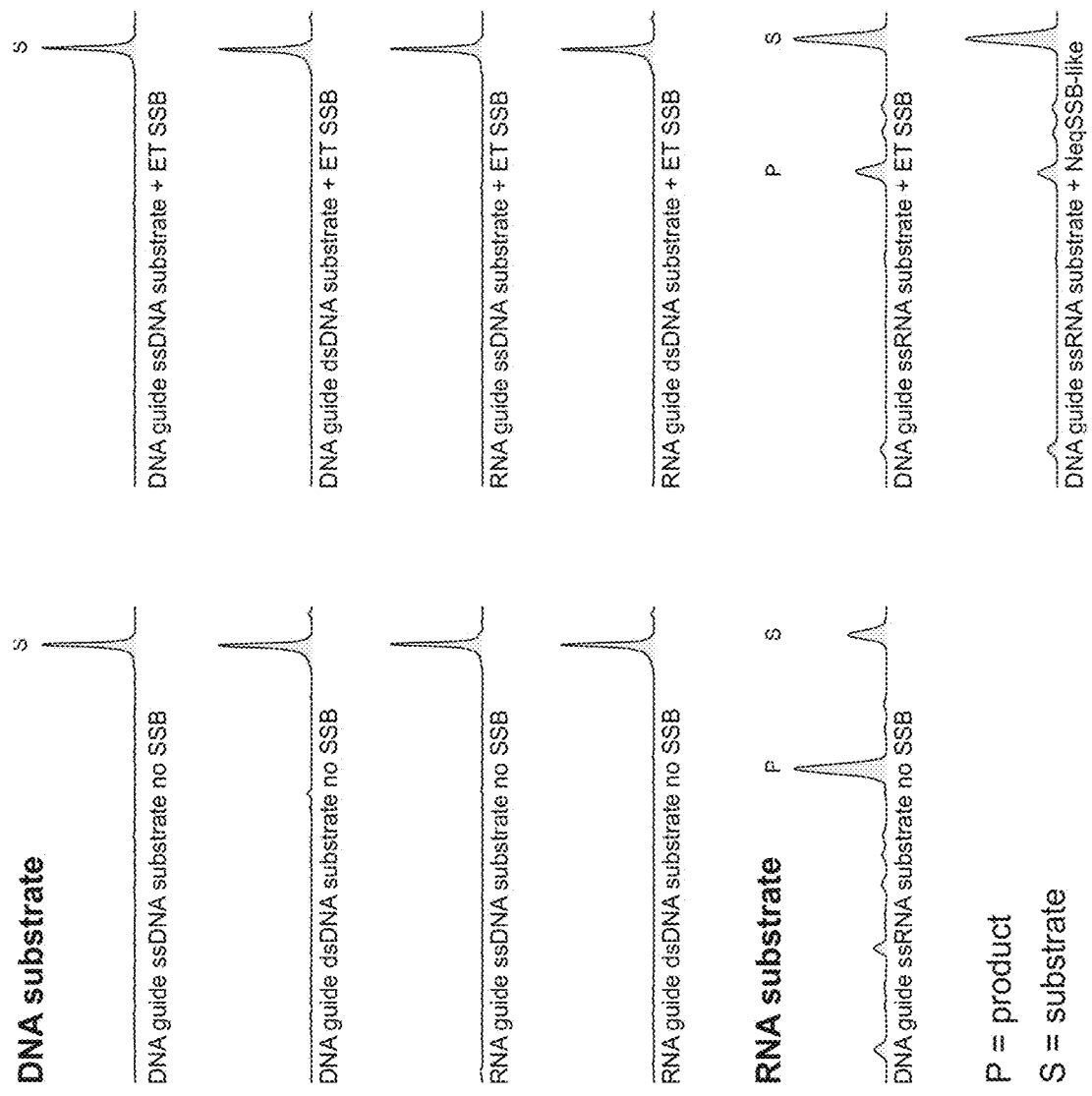

FIG. 7 shows the results of adding a thermostable single strand binding protein to an Argonaute that is not thermostable. NgAgo did not cleave ssDNA or dsDNA either in the presence or absence of SSB. NgAgo did cleave RNA to a limited extent but no difference was detected between reactions containing SSB and reactions where SSB was omitted.

Figure 8:
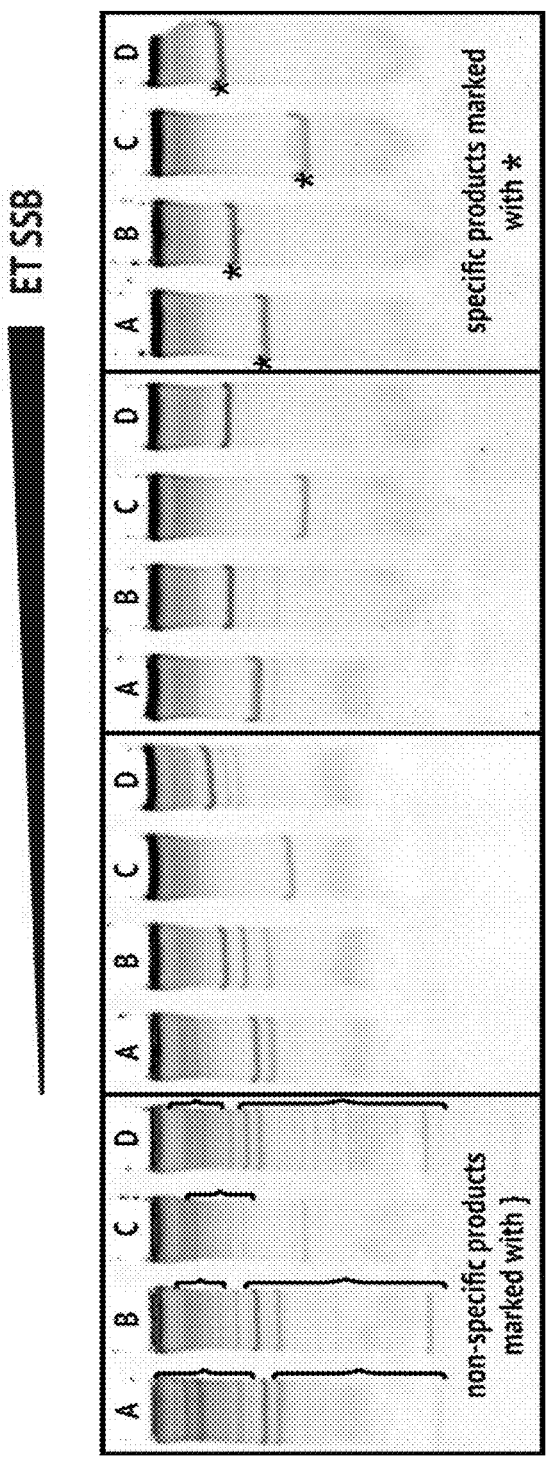

FIG. 8 shows how the addition of a thermostable SSB to thermostable Argonaute (TtAgo) reduces non-specific activity. Four sets of two guides each (A-D) were used to cut specific fragments from circular ϕX174 Virion DNA (New England Biolabs, Ipswich, Mass.). In the absence of thermostable SSB (left panel), several non-specific products (marked with left brackets "}") are also formed due to off-target cleavage. As thermostable SSB was titrated into the reactions (second from left panel to right panel) only the expected specific products (marked with asterisks "*") were observed. From left to right, the concentrations of single stranded binding protein are: 0 nM, 620 nM, 1.2 µM, and 1.9 µM.

DETAILED DESCRIPTION

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein including U.S. Provisional Application Ser. No. 62/526,019, filed on Jun. 28, 2017, are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES.

The term "non-naturally occurring" refers to a composition that does not exist in nature.

Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an epitope tag, a detectable fusion partner, such as a fluorescent protein, β-galactosidase, luciferase, etc., and the like. A fusion protein may have one or more heterologous domains added to the N-terminus, C-terminus, and/or the middle portion of the protein. If two parts of a fusion protein are "heterologous", they are not part of the same protein in its natural state.

In the context of a nucleic acid, the term "non-naturally occurring" refers to a nucleic acid that contains: a) a sequence of nucleotides that is different to a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

Any one or more of the proteins described herein (e.g., the Argonaute protein, SSB, polymerase etc.) may be temperature sensitive or thermostable where, as used herein, the term "temperature sensitive" refers to an enzyme that loses at least 95% of its activity after 10 minutes at a temperature of 65° C., and the term "thermostable" refers to an enzyme that retains at least 95% of its activity after 10 minutes at a temperature of 65° C.

As used herein, the term "Argonaute protein" refers to a polypeptide with at least 80%, at least 90%, at least 95%, or 100% sequence identity to a wild type Argonaute polypeptide (e.g., Argonaute from *Thermus thermophilus*). Argonaute can be an *Aquifex aeolicus*, a *Microsystis aeruginosa*, a *Clostridium bartlettii*, an *Exiguobacterium*, an *Anoxybacillus flavithermus*, a *Halogeometricum borinquense*, a *Halorubrum lacusprofundi*, an *Aromatoleum aromaticum*, a *Thermus thermophilus*, a *Synechococcus*, a *Synechococcus elongatus*, or a *Thermosynechococcus elogatus* Argonaute. Argonaute can be mammalian Argonaute, such as mouse AGO2. Argonaute can refer to the wild-type or a modified form of the Argonaute protein that can comprise an amino acid change such as a deletion, insertion, substitution, variant, mutation, fusion, chimera, or any combination thereof. This term refers to any modified (e.g., shortened, mutated, lengthened) polypeptide sequence or homologue of the Argonaute. An Argonaute can be enzymatically inactive, partially active, constitutively active, fully active, inducibly active and/or more active, (e.g. more than the wild type homologue of the protein or polypeptide). A "thermostable" Argonaute is a protein that remains catalytically active for at least 5 minutes or 10 minutes at elevated temperatures such as above 45° C., 50° C. or 55° C.

As used herein, the term "single-stranded DNA binding protein" and "SSB" refers to a protein that binds to ssDNA. The genomes of most organisms, including bacteria (e.g., *E. coli*), viruses (e.g., herpes viruses) and mammals, encode at least one SSB. SSBs of interest include, but are not limited to, ET SSB, *E. coli* recA, T7 gene 2.5 product (gp2.5), T4 gene 32 product (gp32), *E. coli* SSB, replication protein A (RPA) from archaeal and eukaryotic organisms, *Nanoarchaeum equitans* SSB-like protein, UvrD, RadA, Rad51, phage lambda RedB or Rac prophage RecT. An SSB may be thermostable or mesolabile. An SSB may have at least 80%, at least 90%, at least 95%, or 100% sequence identity to a wild type SSB. The addition of a SSB does not preclude the addition of a second or more SSBs. A "thermostable" SSB is an SSB that retains ssDNA binding ability at elevated temperatures for at least 5 or 10 minutes. Examples of an elevated temperature includes above 45° C. and may be as high as 95° C. An amount of SSB for use in a reaction may be greater than 200 nM, 300 nM, or 400 nM or as much as at least 1.5 uM, 2 uM, or 3 uM. In some embodiments, SSB may be in a molar excess relative to the Argonaute protein. In some embodiments, the Argonaute protein and SSB may be present in the reaction at molar ratio of 1 (Argonaute):1 (SSB) to 1 (Argonaute):100 (SSB), e.g., 1 (Argonaute):5 (SSB) to 1 (Argonaute):30 (SSB), e.g., about 1 (Argonaute): about 15 (SSB), although ratios outside of these ranges can be used.

As used herein, a strand displacing polymerase can be thermostable e.g. est or esu polymerase, archaeal polymerases or mutants thereof which are stable and active above 45° C. for example above 60° C. for example at 70° C. or 75° C.

As used herein, the term "guide DNA" refers to a single-stranded oligonucleotide composed of at least 50% deoxyribonucleotides (e.g., at least 60%, at least 70%, at least 80%, at least 90%, or 100% deoxyribonucleotides). In some embodiments, the guide DNA is synthetic. The guide DNA is capable of directing an Argonaute polypeptide:guide DNA complex to a target polynucleotide. More specifically, the guide DNA is believed to bind an Argonaute protein and to hybridize to a target nucleic acid. Guide molecule nucleotides can be numbered from 5' to 3', with the initial nucleotide being indicated as g1, and subsequent nucleotides being indicated, proceeding 5' to 3', as g2, g3, g4, etc. In one embodiment, the DNA guide length suitable for Argonaute cleavage of dsDNA in the presence of a single strand binding protein may comprise at least 12 nucleotides, for example, having a size range of 12-60 nucleotides, 14-50 nucleotides, 15-40 nucleotides, 16-35 nucleotides, 15-24 nucleotides, or 16-21 nucleotides. In another embodiment, the guide DNA may be greater than 21 nucleotides or at least 24 nucleotides in length. In many embodiments, the guide DNA can be 16-21 nucleotides in length (i.e., 16, 17, 18, 19, 20 or 21 nucleotides). However as illustrated above, shorter or longer guide DNAs may be used in some implementations of the method.

In some embodiments, the guide DNA may comprise a nucleotide sugar modification or a nucleotide substitution. In some embodiments, the nucleotide sugar modification comprises a 2' sugar modification and maybe selected from the group consisting of a 2'-O—$CH_3$, a 2'-F, and a 2'-MOE modification. In other embodiments, the nucleotide substitution comprises one selected from the group consisting of locked nucleic acid (LNA), an unlocked nucleic acid (UNA), deoxyuridine, pseudouridine, 5-methylcytosine, 2-aminopurine, 2,6-diaminopurine, deoxyinosine, 5-hydroxybutynl-2'-deoxyuridine, 8-aza-7-deazaguanosine, and 5-nitroindole. In further embodiments, the guide molecule comprises a sugar modification and a nucleotide substitution. Guide DNAs should have a 5' phosphate.

A DNA guide may be an oligonucleotide or polynucleotide that is synthetic or from a natural source such as genomic DNA, cDNA, extrachromosomal DNA, microbial DNA or viral DNA. The guide DNA is generally single-stranded when used with Argonaute although it may be derived from dsDNA.

As used herein, the term "oligonucleotide" refers to a polymer of nucleotides comprising naturally occurring nucleotides, non-naturally occurring nucleotides, derivatized nucleotides, or a combination thereof. As used herein, the term "complementarity" refers to the ability of nucleotides, or analogues thereof, to form Watson-Crick base pairs. Complementary nucleotide sequences will form Watson-Crick base pairs and non-complementary nucleotide sequences will not.

As used herein, the term "RNA," "RNA molecule," or "ribonucleic acid molecule" refers to a polymer of ribonucleotides.

As used herein, the term "DNA," "DNA molecule," or "deoxyribonucleic acid molecule" refers to a polymer of deoxyribonucleotides. DNA and RNA can be synthesized naturally (e.g., by DNA replication or transcription of DNA, respectively). DNA and RNA can also be chemically synthesized. DNA and RNA can be single-stranded (i.e., ssRNA and ssDNA, respectively) or multi-stranded (e.g., double-stranded, i.e., dsRNA and dsDNA, respectively).

As used herein, the terms "target nucleic acid," "target polynucleotide," and "target nucleotide sequence" refer to a target nucleic acid to be targeted. A target nucleic acid can be a chromosomal sequence or an extrachromosomal sequence, (e.g. an episomal sequence, a minicircle sequence, a plasmid, a mitochondrial sequence, a chloroplast sequence, etc.). A target nucleic acid can be a dsDNA or ssDNA; a target nucleic acid may also be an RNA.

As used herein, the term "isothermal" refers to temperature conditions that do not require active modulation of temperature for a reaction to occur. Insignificant variations in the temperature of a water bath or heating block are within the scope of the meaning of the term isothermal. By way of example, the term "isothermal", may refer to reaction conditions that do not require a heat denaturation step after the reaction has started. More specifically, isothermal methods do not involve thermocycling, i.e., cycling between a denaturation temperature of above 90° C. and an annealing/extension temperature. Isothermal conditions usually involve incubation at a temperature that is below 90° C. for a period of time (e.g., 5 minutes to 12 hours or more). In one embodiment, isothermal amplification reactions were performed at a temperature in the range of 30° C.-75° C., for example, 40° C.–60° C.

As used herein, the term "composition" refers to a combination of reagents that may contain other reagents, e.g., glycerol, salt, dNTPs, etc., in addition to those listed. A composition may be in any form, e.g., aqueous or lyophilized, and may be at any state (e.g., frozen or in liquid form).

As used herein, "proximal" refers to a distance of 1-1000 nucleotides (from the guide DNA hybridized to the target DNA), for example, 1-16 nucleotides.

The state of the art holds that prokaryotic DNA guided Argonaute enzymes are unable digest dsDNA substrates using guided nuclease cleavage (see for example, Swarts, et al. Nature 507, 258-261 (2014), Enghiad, et al, ACS Synth Biol 6, 752-757 (2017)). Embodiments of the method provide the surprising benefit of adding a SSB to overcome this limitation. In these embodiments, addition of helicase or recombinase is not required in addition to the single strand binding protein to observe the enhanced cleavage efficacy and specificity. The claimed composition provides an enzyme mixture that is capable of cleaving linear, open circular and negatively or positively supercoiled double-stranded substrates. Examples of Argonautes that show this beneficial effect when combined with SSB are thermostable DNA guided Argonautes that are archaeal or prokaryotic for example, the archaeal Argonaute (PfAgo) and the prokaryotic Argonaute (TtAgo). Examples of dsDNA substrates include plasmids. FIG. 1A-1D illustrates the dramatic improvement in cleavage of substrate dsDNA regardless of GC content in the presence of single strand binding protein. A dramatic improvement is also observed in cleavage of ssDNA substrates having a GC content of greater than 30%. The cleavage or nicking reaction may be completed within 4 hours, usually within 1 hour or for example within 30 minutes.

Figures 1A, 1B, 1C, 1D:
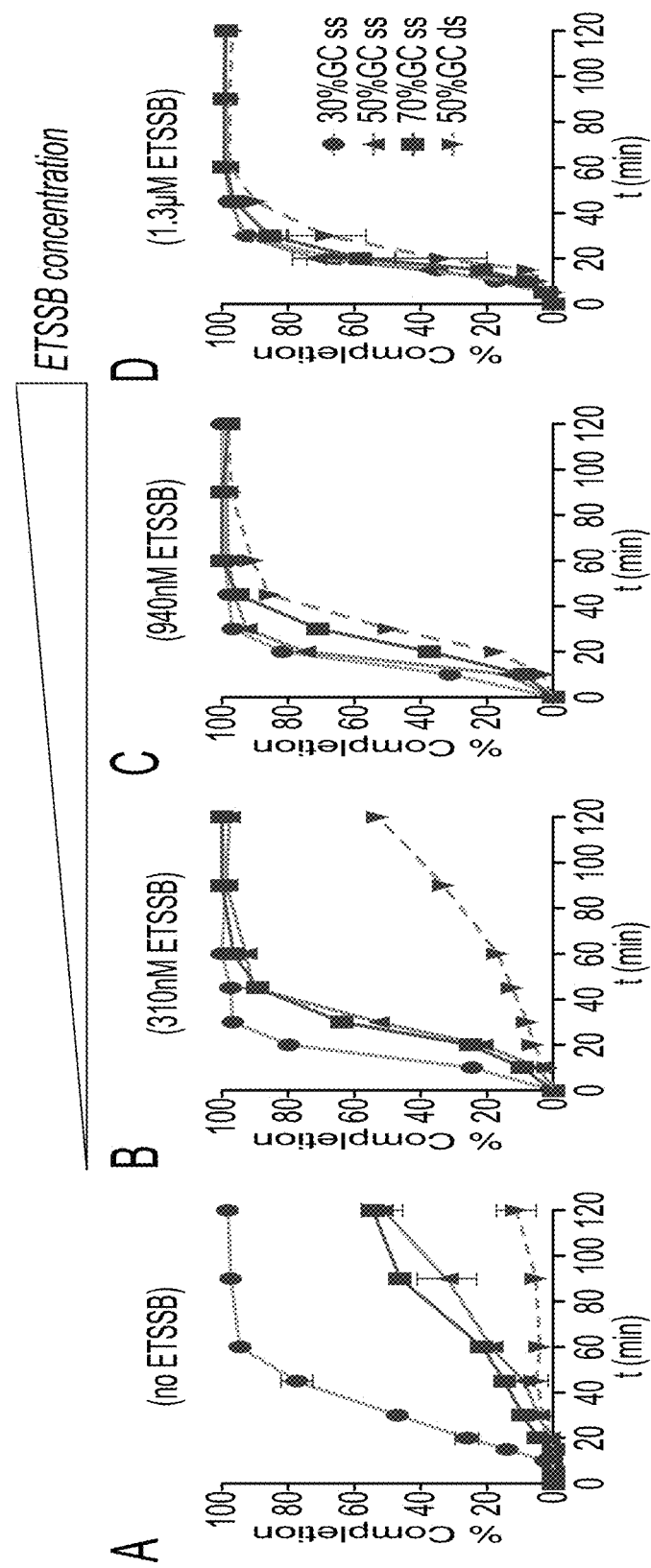
FIG. 1A-1D shows data demonstrating that a SSB greatly enhances the guided cleavage activity of a thermostable Argonaute. Results are shown for bacterial *Therma thermophilus* Argonaute (TtAgo), and similar results were also obtained using the same concentrations of ET SSB (#2401S, New England Biolabs, Ipswich, Mass.) with archaeal *Pyrococcus furiosus* Argonaute (PfAgo). This data shows that the addition of ET SSB improves the activity of Argonaute proteins on ssDNA substrates and allows Argonaute to cleave dsDNA substrates.
Figures 2A, 2B, 2C:
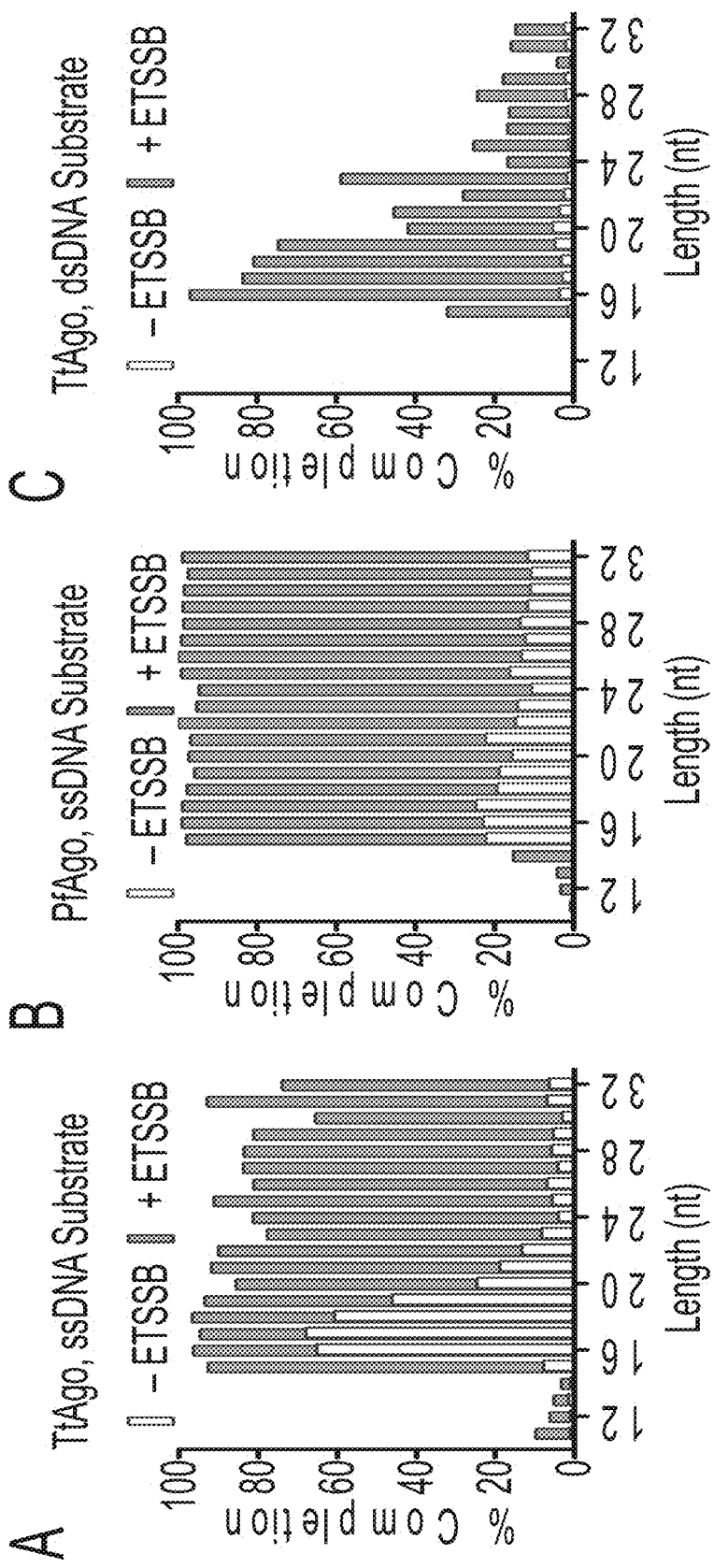
FIG. 2A-2C shows that the effects of various lengths of guide DNA on cleavage of ssDNA and dsDNA in the presence and absence of SSB.

Another surprising benefit identified herein is the increased specificity of Argonaute cleavage when a thermostable DNA guided Argonaute is combined with a SSB. Generally, site-specific nucleases have "star" activity. This means that specificity of cleavage can be a problem. FIG. 2A-2C illustrates that the percentage completion of cleavage of ssDNA or dsDNA substrate by the thermostable DNA guided Argonaute is greatly increased in the presence of single strand binding protein. The double strand DNA cleavage is sensitive to the length of the guide DNA however where a guide of length 16-21 nucleotide provides the maximum cleavage. FIG. 8 shows the star activity of TtAgo which leads to production of off-target nonspecific species. This star activity is suppressed by the SSB which to creation of only the desired, specific product.

Figure 3:
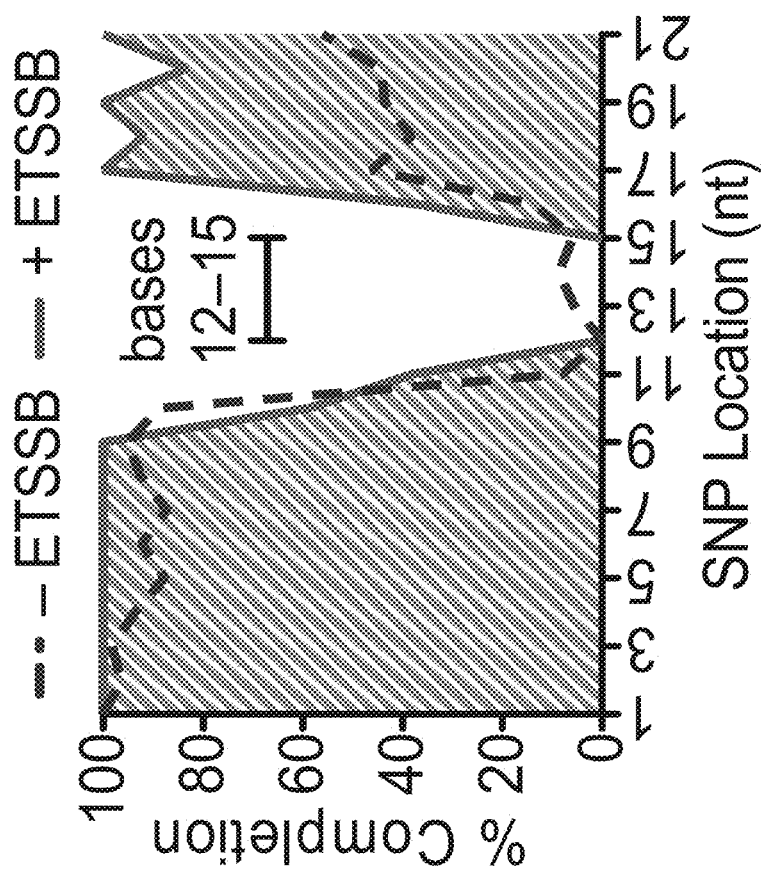
FIG. 3 shows that in addition to relaxing the guide length preference as demonstrated in FIG. 2A-2C, the addition of ET SSB also enhances sensitivity of TtAgo to mismatches falling within the 12-15 region of the guide. This feature can be exploited for potential applications which require a greater degree of specificity in relation to the guide/substrate complex, such as in methods for SNP or mutation detection, or for depletion of certain nucleic acid substrates from a mixture.

Another surprising benefit identified herein is that in the presence of thermostable SSB, the thermostable DNA guided Argonaute cleavage shows enhanced sensitivity to single nucleotide mutations falling within the 12-15 nucleotide region of the guide (FIG. 3). This improves its utility in SNP discrimination. The use of thermostable SSB with prokaryotic Argonaute such as TtAgo could enable the discrimination of SNPs and mutations in ssDNA and dsDNA targets.

A combination of thermostable DNA guided Argonaute protein and thermostable SSB can be used to deplete specific sequences from a DNA library. In one example, a thermostable SSB can be combined with a prokaryotic thermostable Argonaute such as TtAgo to remove high-abundance sequences through targeted degradation. These high-abundance sequences could include dimers or multimers of library preparation adaptors and primers, high-copy-number sequences or genes, or wild-type or host DNA where the mutant or rare commensal species or pathogen is the target of interest. For similar enrichment purposes, a catalytic prokaryotic Argonaute mutant—such as TtAgo with one or more of the following residues mutated (D478, E512, D546, D660), or another mutation which disrupts the endonuclease activity of the PIWI domain, or through the removal of cofactors required for catalytic activity by specific buffer formulation (such as high EDTA to remove catalytic $Mg2+$)—in a formulation which may or may not contain thermostable SSB, can be used to target and pull down, via some engineered affinity handle (hexahistidine tag, binding domain fusion, chemical modification), sequences of interest as directed by the guide oligonucleotide sequence. These enriched sequences might represent rare species in a large pool of other sequences, specific mutation sequences, sequences from commensal organisms, or viral or pathogenic sequences in a sample.

TtAgo with thermostable SSB could be employed to improve the diagnostic specificity and capabilities of nucleic acid amplification tests by eliminating targets of specific strains or sequence which may overlap or interfere with the overall detection platform.

The addition of single strand binding protein to thermostable Argonautes that permits cleavage of dsDNA in addition to ssDNA enables the possibility of substituting RNA guided Cas9 for the DNA guided thermostable Argonaute as an efficient and specific in vitro reagent for targeted cleavage of DNA.

Figure 4:
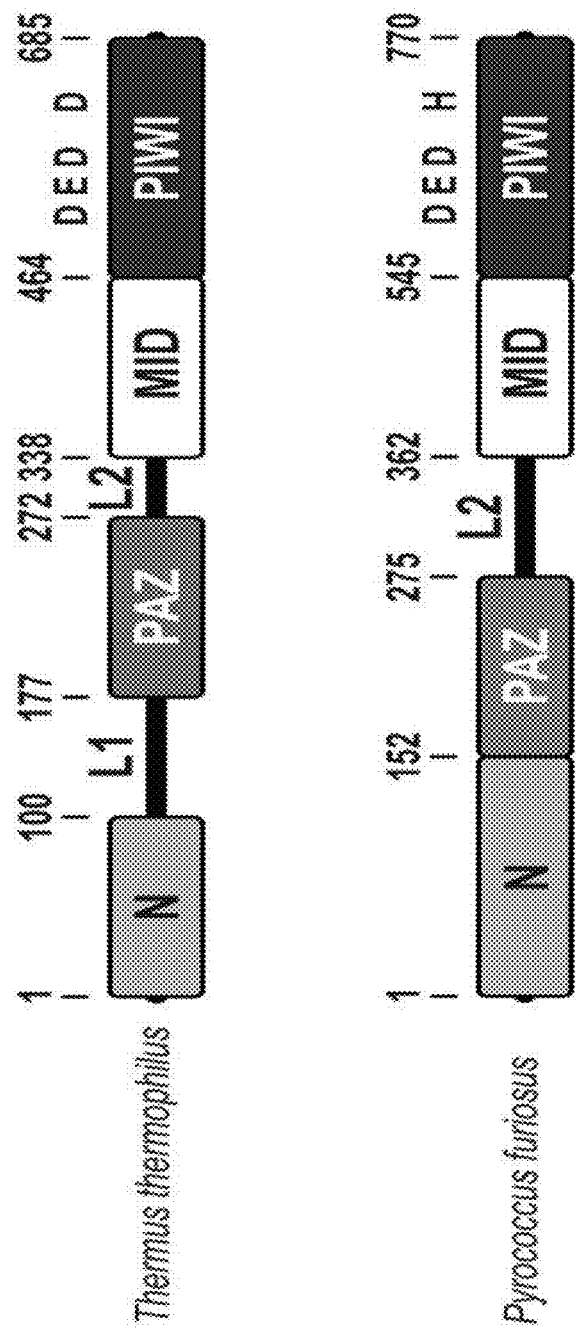
FIG. 4 shows the common structure of DNA guided DNA cleaving Argonaute proteins from thermostable bacteria and archaea. Argonautes from these different sources gave similar results in the presence of a SSB. It is therefore expected that the effect is general for any SSB and any DNA guided Argonaute protein with DNA cleaving activity.

As shown in FIG. 4, thermostable DNA guided Argonautes are structurally similar and, as such, it is expected that SSBs will have an effect on this group of Argonaute proteins. Suitable Argonautes include, but are not limited to the TtAgo, PfAgo and *Methanocaldococcus jannaschii* Argonaute (MjAgo). Thermostable Argonaute proteins are generally derived from a thermophilic organism.

The composition may further comprise a DNA substrate that comprises a target sequence that is complementary to the synthetic guide DNA. The DNA substrate may be dsDNA or ssDNA (which term is intended to include denatured dsDNA). If dsDNA is used, it may be genomic DNA from any organism (e.g., prokaryotic DNA, eukaryotic (animal or plant) DNA, or an amplification product thereof. In some embodiments, the dsDNA may be from the genome of a mammal.

A DNA substrate is typically cleaved at a phosphodiester bond across from nucleotide position 10 and 11 of the guide DNA. In some embodiments at least positions g1 to g16 may be complementary to a target sequence in a substrate, although a number of mismatches (e.g., one or two mismatches) may be tolerated. As noted above, in some embodiments, nucleotides 12-15 (g12 to g15) of the guide DNA should be perfectly complementary to the target sequence. In embodiments that employ a longer guide DNA, the nucleotides at the 3' end of the guide DNA (e.g., at least 8, 9 or 10 nucleotides) may be perfectly complementary to a target sequence in the substrate.

In some embodiments, the composition may be an aqueous solution that comprises a non-naturally occurring buffering agent at a concentration of 1 mM to about 200 mM, salt (e.g., KCl or NaCl), a divalent cation (e.g., $Mg^{2+}$ or $Mn^{2+}$). In these embodiments, the composition can have a pH of about 7 to about 8.8, such as 7.4 to 7.5. In some embodiments, the composition may further contain a reducing agent (e.g., dithiothreitol), a detergent, glycerol, sugar or dNTPs, as needed.

In certain embodiments, the composition may further comprise a strand-displacing polymerase. In these embodiments, the polymerase may be est polymerase or a variant thereof, although many strand-displacing polymerases are known and could be used. Strand-displacing polymerases are able to displace one or more nucleotides, such as at least 10 or 100 or more nucleotides that are downstream from the enzyme. In some embodiments, the strand displacing polymerase is stable and active at a temperature of at least 50° C. or at least 55° C. (including the strand displacing activity).

The composition described above may be employed in a variety of methods, particularly in vitro (i.e., cell free) methods, including, but not limited to digestion, depletion, or enrichment methods; or as an initiator of amplification; for purposes that include recognizing a nucleic acid for editing; detecting nucleic acid sequence via binding to Argonaute; and sequencing of target nucleic acids.

In some embodiment, the method may be applied to cleaving a substrate DNA at a target sequence. In some embodiments, the method may comprise combining an Argonaute protein, an SSB, a guide DNA, and a DNA substrate that comprises a target sequence that is complementary to at least part of the synthetic guide DNA, to produce a reaction mix; and (b) incubating the reaction mix to cleave the substrate DNA at the target sequence. In some embodiments, cleavage is accomplished by incubating the sample at a template in the range of 45° C. to 50° C. or a temperature of at least 50° C. In some embodiments, cleavage is accomplished by incubating the sample at a temperature of above 55° C., 60° C., e.g., 60° C. to 75° C., at about 65° C., or in the range of 80° C. to 95° C. In many embodiments, the reaction mix may be incubated for a period of time in the range of 5 minutes to 2 hours. In some embodiments, substantially complete cleavage may be achieved within 1 hour or 30 minutes.

As noted above, the substrate can be a ssDNA substrate or a dsDNA substrate. In embodiments that employ a dsDNA substrate, step (b) of the method results in cleavage of one strand of the dsDNA substrate (i.e., to produce a nick). If a dsDNA substrate is used, then the method further comprises cleaving the opposing strand of the substrate at the complement of the target sequence, thereby creating double-stranded break in the target sequence. As would be apparent, this may be done using Argonaute protein/guide DNA that targets cleavage of opposite strands of the dsDNA substrate.

In another embodiment, a method is provided for copying a nucleic acid substrate. This method may include one or more of the following steps: combining a thermostable DNA guided Argonaute protein, a thermostable SSB, the nucleic acid substrate that comprises a target sequence, a strand-displacing polymerase, and a guide DNA that is complementary to the target sequence, to produce a reaction mix; incubating the reaction mix so that a strand of the nucleic acid substrate provides a template for the polymerase, and extending (i) the 3' end of the guide DNA (ii) a separate primer that hybridizes to a site that is proximal to the target sequence or (iii) the 3' end formed by the Argonaute induced nick; and copying the nucleic acid substrate.

The Argonaute protein is catalytically inactive in (i) or (ii). Alternatively, the Argonaute protein is catalytically active in (ii) or (iii).

While not wishing to be limited by theory, the SSB facilitate strand may facilitate invasion of the nucleic acid substrate if it is double stranded by the guide DNA or separate primer and the 3' end of the guide DNA or separate primer can then be extended using the double-stranded target sequence as a template. In Argonaute protein/guide DNA complexes that contain "longer" guide DNAs, the 3' end of the guide DNA extends out of the complex and is accessible by the DNA polymerase. In effect, the guide DNA acts as a primer in this reaction. Alternative embodiments can be implemented using a separate primer. This method may be done using a catalytically active or inactive Argonaute protein (i.e., the method may be done with or without cleaving the substrate). As illustrated in FIG. 5, in some embodiments the reaction mix may further comprise a second guide DNA that is at least 24 nucleotides in length (or a separate primer), wherein the second guide DNA (or separate primer) is complementary to a second target sequence that is downstream from and on the opposite strand to the target sequence of the other guide DNA. In these embodiments, the incubation step results in extension of the second guide DNA or primer using the opposing strand as a template, thereby copying both strands of the DNA substrate. Because the primer extension product produced by extending one of the guide DNAs/primers recreates a double-stranded substrate for the other Argonaute protein/guide DNA complex, this embodiment of the method results in exponential amplification of a sequence in the substrate under isothermal conditions. In some embodiments, a catalytically active Argonaute proteins may generate an amplification product of defined length. The length of the amplified fragment may be 50 bp-10 kb in length, although fragments outside of this range are envisioned.

In some embodiments, the method may be applied to identifying a polymorphism. This method may comprise one or more of the following steps: (a) combining an Argonaute protein, an SSB, an allele-specific guide DNA, and a double strand DNA substrate that has a single or multiple nucleotide polymorphisms in the region corresponding to nucleotides 12-15 of the guide DNA, to produce a reaction mix; (b) incubating the reaction mix to cleave a strand of the DNA substrate; and (c) detecting cleavage of the substrate, wherein cleavage indicates the allele of the polymorphism. The detection step may be done in a variety of different ways. For example, detection could be through amplification of cleaved product, ligation to reporter molecule, or readout of specific binding even without cleavage. In this method, the allele of the polymorphism in the substrate (e.g., genomic DNA) may be unknown at the time at which the test is done. Because the guide DNA is allele-specific (i.e., may contain a sequence at nucleotides 12-15 that corresponds to the sequence of a particular allele of the polymorphism), cleavage of the substrate indicates the allele of the polymorphism that is present in the substrate. As would be apparent, the substrate may be a dsDNA substrate (e.g., genomic DNA or a double-stranded amplification product). However, in some embodiments, polymorphisms in a ssDNA substrate (e.g., a denatured substrate) may be detected where the use of the single strand binding protein in this reaction is optional.

Kits

Also provided by the present disclosure are kits for practicing the subject method as described above. In certain embodiments, the kit may contain (a) an Argonaute protein and (b) a SSB. These components may be in separate containers or mixed together in the same container. The kit may contain a buffer, e.g., in concentrated form (e.g., a 5× or 10× concentrate) and, optionally any of the components described above, e.g., polymerase, dNTPs, guide DNAs, etc. The components of the kit may be combined in one container, or each component may be in its own container. Embodiments of the methods described herein may be performed in a single step by combining the components with the substrate and incubating at a single preselected temperature for a time period as described above. Further details of the components of this kit are described above.

In addition to above-mentioned components, the subject kit further includes instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In order to further illustrate the present invention, the following specific examples are given with the understanding that they are being offered to illustrate the present invention and should not be construed in any way as limiting its scope.

EXAMPLES

Aspects of the present teachings can be further understood in light of the following examples, which should not be construed as limiting the scope of the present teachings in any way.

Example 1: The Addition of SSB Improves Activity of TtAgo on ssDNA Substrate from Low to High GC Content, and on dsDNA Substrate Synthetic DNA and RNA oligonucleotide substrates and guides were purchased from Integrated DNA Technologies. ssDNA and dsDNA and RNA oligonucleotide substrates were ordered with a 5' FAM modification, with double-stranded substrates being modified on the same strand corresponding to the single-stranded substrates. DNA and RNA oligonucleotide guides were phosphorylated using T4 Polynucleotide Kinase (New England Biolabs, Ipswich, Mass.) according to the supplier-provided protocol. PNK was thermally denatured by incubation at 65° C. for 20 minutes following the phosphorylation reaction.

Reactions were prepared by mixing a DNA guide:Argonaute:target in a 1:2:1 molar ratio in ThermoPol® Reaction Buffer (New England Biolabs, Ipswich, Mass.). ET SSB was added to reactions at concentrations varying from low nM to low μM. The reactions were incubated at 73° C. for 1 hour in the case of TtAgo, and 90° C. for 1.5 hours in the case of PfAgo. Reactions were halted at various time points by rapid cooling followed by degradation of Argonaute protein by incubation with proteinase K (New England Biolabs, Ipswich, Mass.) for 30 minutes at 40° C. Products were diluted with water to a concentration of approximately 4 nM and analyzed by capillary electrophoresis.

The results are shown in FIG. 1A-1D. The addition of a SSB causes complete cleavage of dsDNA within the same time frame as ssDNA with no evident bias of base composition. In the presence of SSB, the reaction rate for AT rich ssDNA is doubled. There is a significant and important reduction in bias in cleaving ssDNA and cleavage of dsDNA occurs in the same time frame and amount as the ssDNA when compared with results for Argonaute cleavage in the absence of the SSB.

Example 2: Testing Effects of DNA Guide Lengths of Varying Sizes on Argonaute Activity Synthetic ssDNA and dsDNA oligonucleotide substrates as well as ssDNA guides of varying lengths were purchased from Integrated DNA Technologies (Coralville, Iowa). Guides were phosphorylated using T4 Polynucleotide Kinase according to the supplier-provided protocol. PNK was thermally denatured by incubation at 65° C. for 20 minutes following the phosphorylation reaction.

The reactions were prepared as described in Example 1 and included 1.3 μM ET SSB for all reactions. The results are shown in FIG. 2A-2C.

Example 3: Addition of ET SSB to TtAgo Increases SNP Specificity

Synthetic ssDNA and dsDNA oligonucleotide substrates as well as ssDNA 21 nucleotide guides containing point mutations at every base throughout were purchased from Integrated DNA Technologies. Guides were phosphorylated using T4 Polynucleotide Kinase according to the supplier-provided protocol. PNK was thermally denatured by incubation at 65° C. for 20 minutes following the phosphorylation reaction.

The reactions were prepared as described in Example 1 and included 1.3 μM ET SSB in all reactions.

Illustrative results are shown in FIG. 3. FIG. 3 shows that cleavage was particularly sensitive to mismatches between nucleotide 11 and 15 in the guide DNA. It was observed that the main region of the guide that determines specificity was in the region of bases 12-15. Any mutations in this region decreased Argonaute activity. However, in the case of adding ET SSB to the Argonaute, activity was completely eliminated, while some residual activity remains when Argonaute is used without ET SSB. Thus, the ET SSB enhances sensitivity to SNPs falling within this 12-15 region and can identify single nucleotide differences. Additionally, the addition of ET SSB removes Argonaute sensitivity with regards to mutations occurring downstream (i.e. 3') of the 12-15 region. Without ET SSB, approximately 50% activity is seen when a mutation falls in the 16-21 region. However, when ET SSB is used in conjunction with Argonaute, full activity is observed. This effect is beneficial because it allows targeting of SNPs to the sensitive 12-15 region with a high degree of confidence, whereas without ET SSB, one may not be entirely sure the decrease in activity is due to a mutation in that specific region. This will be crucial for SNP detection.

Example 4: Argonaute-Mediated Amplification Method

In two separate reactions, Ago is complexed in ThermoPol buffer with one of two 24 nucleotides guides by incubating at 75° C. for at least 20 minutes. The guide is kept in slight molar excess to Ago to ensure complete association of Ago with the guide. The two guides are complementary to opposite strands and directionally oppose each other in an inward fashion on a dsDNA substrate. The Ago-guide complexes are then mixed with dsDNA substrate in ThermoPol buffer, along with Aux—such as ET SSB—at an approximately 40 times molar excess, and an SDPol-such as Bst 3.0 DNA Polymerase (New England Biolabs, Ipswich, Mass.)—at approximately 0.2-2.0 U/µL. The reaction is then incubated at 65° C.-70° C. to initiate Ago binding and polymerase extension. This method is schematically illustrated in FIG. 5.

Example 5: ET SSB Enhances/Enables Activity on Double-Stranded Substrates of Prokaryotic Argonautes MetaAgo-1 and MetaAgo-2 Derived from Metagenomic Material from a Hot Spring MetaAgo-1 and -2 were used in equimolar amounts to fluorescently labeled targets, and 5'-phosphorylated 21 nucleotide DNA guide was used at 5× molar excess to MetaAgo-1 and -2. 400 ng of ET SSB was added to reactions where specified. Reactions were carried out across a range of temperatures for 60 minutes. Reactions were halted by rapid cooling and subsequent digestion with proteinase K (New England Biolabs, Ipswich, Mass.) at 37° C. for 30 minutes. Reaction were analyzed by capillary electrophoresis performed on an Applied Biosystems 3730xl DNA 426 Analyzer, 36 cm capillary array with 5 seconds injection time. Peaks were sized according to the GeneScan™ 120 LIZ™ dye Size Standard (Thermo Fisher Scientific, Waltham, Mass.). The results are shown in FIG. 6A-6H.

Example 6: ET SSB does not Enhance the Activity of *Natronobacterium gregoryi* Argonaute (NgAgo) on ssRNA or Enable Cutting of DNA Substrates A recombinant NgAgo was expressed in *E. coli* and purified by IMAC FPLC using a 5 mL HisTrap® FF column on an ÄKTA® FPLC (GE Healthcare Life Sciences, Marlborough, Mass.) under denaturing conditions with 6 M guanidine hydrochloride. Purified NgAgo was dialyzed into 10 mM Tris-HCl pH 7.4 @ 25° C., 100 mM potassium chloride; 1 mM DTT, 0.1 mM EDTA, 50% glycerol and stored at −20° C. until use. NgAgo was used to cut 98 nucleotide DNA or 60 nucleotide RNA substrates labeled with a 5'-FAM (carboxyfluorescein). Successful cleavage would result in 60 nucleotide or 40 nucleotide fluorescently labeled products for DNA and RNA substrates, respectively. NgAgo was used in 50× molar excess over fluorescently labeled targets, and 5'-phosphorylated 21 nucleotide DNA guide was used at 1× molar equivalent to NgAgo. Reactions were allowed to progress at 37° C. for 16 hours before being analyzed by capillary electrophoresis performed on an Applied Biosystems 3730xl DNA 426 Analyzer, 36 cm capillary array with 5 seconds injection time. Peaks were sized according to the GeneScan 120 LIZ dye Size Standard. No DNA cleavage was observed. Some specific cleavage of ssRNA was observed (product marked with "P" in FIG. 7). 400 ng of ET SSB was added to reactions where specified. The results are shown in FIG. 7. Thermostable SSB did not enhance either activity on DNA or RNA.

Example 8: Addition of ET SSB to TtAgo Reduces Star-Activity

The addition of thermostable SSB to TtAgo reduces non-specific activity. TtAgo was used in 30× molar excess over substrate. 5'-phosphorylated 17 nt DNA guides were used in 6× molar excess over Argonaute. In each pair (A-D) two guides are combined in an equimolar ratio. 0-14 (0-500 ng) of ET SSB were titrated into reactions (from left to right in the figure below). Guides were pre-loaded into Argonaute by incubation at 75° C. for 20 minutes before addition of the substrate. Upon addition of the substrate, reactions were incubated at 75° C. for 5 hours, halted by rapid cooling and addition of Purple Loading Dye with SDS (New England Biolabs, Ipswich, Mass.) to 1× concentration, and analyzed by SDS-PAGE on Novex 20% polyacrylamide gels (Thermo Fisher Scientific, Waltham, Mass.). Gels were stained after running with 1× SYBR™ Gold (Invitrogen, Thermo Fisher Scientific). The results are shown in FIG. 8.

What is claimed is:

1. A composition comprising a bacterial thermostable DNA guided Argonaute protein, an archaeal thermostable single-stranded DNA binding protein (SSB), a guide DNA, and a nucleic acid substrate that comprises a target sequence that is complementary to the guide DNA.

2. The composition of claim 1, wherein the guide DNA is 16-21 nucleotides in length.

3. The composition of claim 1, wherein the guide DNA is at least 22 nucleotides in length.

4. The composition of claim 3, further comprising a strand-displacing polymerase.

5. The composition according to claim 1, wherein the nucleic acid substrate is a double-stranded DNA (dsDNA) substrate.

6. The composition according to claim 1, wherein the thermostable single-stranded DNA binding protein (SSB) is an extreme thermostable single-stranded DNA binding protein (ET SSB).

7. The composition according to claim 1, wherein the bacterial DNA guided Argonaute protein is an *Aquifex aeolicus*, a *Microsystis aeruginosa*, a *Clostridium bartlettii*, an *Exiguobacterium*, an *Anoxybacillus flavithermus*, an *Aromatoleum aromaticum*, a *Thermus thermophilus*, a *Synechococcus*, a *Synechococcus elongatus*, or a *Thermosynechococcus elongatus* Argonaute.

8. A method for cleaving a nucleic acid substrate at a target sequence, comprising:
(a) combining a bacterial thermostable DNA guided Argonaute protein, an archaeal thermostable SSB, a guide DNA and the nucleic acid substrate that comprises a target sequence that is complementary to at least part of the guide DNA, to produce a reaction mix;

(b) incubating the reaction mix under conditions suitable for cleaving the nucleic acid substrate at the target sequence; and (c) cleaving the nucleic acid substrate.

9. The method of claim 8, wherein the nucleic acid substrate is a double-stranded DNA (dsDNA) substrate and step (b) results in a nick in the dsDNA substrate after cleavage of one strand.

10. The method of claim 9, wherein the method further comprises nicking the second strand of the dsDNA substrate at a site on a strand that is complementary to or proximate to the target sequence but not the guide DNA.

11. The method according to claim 10, wherein the cleavage of the substrate is substantially complete within 1 hour.

12. The method according to claim 8, wherein the nucleic acid substrate is eukaryotic genomic dsDNA.

13. The method according to claim 8, wherein cleaving in (c) is performed under isothermal conditions.

14. A method for copying a substrate DNA, comprising:

(a) combining a bacterial thermostable DNA guided Argonaute protein, an archaeal thermostable single-stranded DNA binding protein (SSB), a double-stranded DNA (dsDNA) substrate that comprises a target sequence, a strand-displacing polymerase, and a guide DNA that is complementary to the target sequence, to produce a reaction mix; and (b) incubating the reaction mix, so that a strand of the DNA substrate provides a template for the polymerase, and extending (i) the 3' end of the guide DNA (ii) a separate primer that hybridizes to a site that is proximal to the target sequence or (iii) the 3' end formed by the Argonaute induced nick; and (c) copying the nucleic acid substrate.

15. The method of claim 14, wherein the Argonaute protein is catalytically inactive in (i) or (ii).

16. The method of claim 14, wherein the Argonaute protein is catalytically active in (ii) or (iii).

17. The method of claim 14, wherein (b) is an isothermal reaction.

18. The method according to claim 14, wherein the guide DNA is at least 24 nucleotides.

19. The method of claim 14, wherein the reaction mix further comprises a second guide DNA complementary to a second target sequence that is proximate to the opposite strand to a first target sequence, and wherein the incubation step results in extension of the second guide DNA using the opposing strand as a template, thereby resulting in copying of both strands of the nucleic acid substrate between the first and the second guide DNA.

20. A method for identifying a polymorphism, comprising:

(a) combining a bacterial thermostable DNA guided Argonaute protein, an archaeal thermostable single-stranded DNA binding protein (SSB), an allele-specific guide DNA, and a nucleic acid substrate that has a polymorphism in the region corresponding to nucleotides 12-15 of the guide DNA, to produce a reaction mix;

(b) incubating the reaction mix to cleave the nucleic acid substrate; and (c) detecting cleavage of the substrate, wherein cleavage indicates the allele of the polymorphism.

21. The method of claim 20, wherein the nucleic acid substrate is a double-stranded DNA (dsDNA) substrate.

22. A method according to claim 20, wherein the guide DNA hybridizes with the nucleic acid substrate.

23. A non-naturally occurring, preparation comprising an archaeal thermostable DNA guided Argonaute protein and a single-stranded DNA binding protein (SSB), a guide DNA, and a nucleic acid substrate that comprises a target sequence that is complementary to the guide DNA, wherein the SSB is a bacterial thermostable SSB, a viral SSB, or a mammalian SSB.

* * * * *